United States Patent
Webb

(10) Patent No.: US 8,579,971 B2
(45) Date of Patent: Nov. 12, 2013

(54) INFLATABLE INTRA OCULAR LENS/LENS RETAINER

(76) Inventor: Garth T. Webb, Surrey (CA)

(*) Notice: Subject to any disclaimer, the term of this patent is extended or adjusted under 35 U.S.C. 154(b) by 502 days.

(21) Appl. No.: 12/671,573

(22) PCT Filed: Aug. 12, 2008

(86) PCT No.: PCT/CA2008/001456
§ 371 (c)(1),
(2), (4) Date: Feb. 3, 2010

(87) PCT Pub. No.: WO2009/021327
PCT Pub. Date: Feb. 19, 2009

(65) Prior Publication Data
US 2011/0224788 A1   Sep. 15, 2011

Related U.S. Application Data

(60) Provisional application No. 60/955,591, filed on Aug. 13, 2007, provisional application No. 60/985,376, filed on Nov. 5, 2007, provisional application No. 61/051,075, filed on May 7, 2008.

(51) Int. Cl.
*A61F 2/16* (2006.01)

(52) U.S. Cl.
USPC ....... 623/6.13; 623/6.37; 623/6.38; 623/6.39; 623/6.4

(58) Field of Classification Search
USPC ................. 623/6.13, 6.18, 6.37–6.4, 6.49
See application file for complete search history.

(56) References Cited

U.S. PATENT DOCUMENTS

| 4,585,457 A * | 4/1986 | Kalb ................... 623/6.13 |
| 4,664,666 A | 5/1987 | Barrett |
| 4,676,792 A | 6/1987 | Praeger |

(Continued)

FOREIGN PATENT DOCUMENTS

| CA | 2630781 | 5/2007 |
| CA | 2631261 | 5/2007 |

(Continued)

OTHER PUBLICATIONS

International Search Report issued in respect of Patent Cooperation Treaty Patent Application No. PCT/CA2008/001456 filed Aug. 12, 2008 (Published Feb. 19, 2009 under Publication No. WO 2009/021327).

(Continued)

*Primary Examiner* — David H Willse
*Assistant Examiner* — Javier Blanco
(74) *Attorney, Agent, or Firm* — Bruce M. Green; Oyen Wiggs Green & Mutala LLP

(57) ABSTRACT

The invention provides for an inflatable intra ocular lens/lens retainer or a system of inflatable intra ocular lens/lens retainers, which are fitted into an aphakic eye, to substantially occupy the space previously held by the crystalline lens to retain and secure the position of delicate intra ocular structures of the eye. The inflatable lens/lens retainer may also be used suspend optical interfaces along the visual axis of the eye. The inflatable intra ocular lens/lens retainer may be pressed against residual elements of the lens capsule to re-establish accommodation. In the absence of a lens capsule, the inflatable intra ocular lens/lens retainer may be compressed directly by the ciliary muscle to alter the refractive state of the eye.

20 Claims, 15 Drawing Sheets

(56) References Cited

U.S. PATENT DOCUMENTS

| | | |
|---|---|---|
| 4,709,996 A | 12/1987 | Michelson |
| 4,822,360 A | 4/1989 | Deacon |
| 5,133,747 A | 7/1992 | Feaster |
| 5,152,788 A | 10/1992 | Isaacson et al. |
| 5,213,579 A | 5/1993 | Yamada et al. |
| 6,027,531 A | 2/2000 | Tassignon |
| 7,137,994 B2 | 11/2006 | Eugene de Juan et al. |
| 2005/0085907 A1 | 4/2005 | Hanna |
| 2007/0123981 A1 | 5/2007 | Tassignon |

FOREIGN PATENT DOCUMENTS

| | | |
|---|---|---|
| CA | 2629884 | 6/2007 |
| EP | 0202049 | 11/1986 |
| EP | 0356050 A1 | 2/1990 |
| JP | 4-224746 A | 8/1992 |
| WO | 9011736 | 10/1990 |
| WO | 0004849 | 2/2000 |
| WO | 2004/010904 A1 | 2/2004 |
| WO | 2007011879 | 1/2007 |
| WO | 2008024766 | 2/2008 |

OTHER PUBLICATIONS

International Search Report issued in respect of Patent Cooperation Treaty Patent Application No. PCT/CA2008/001455 filed Aug. 12, 2008 (Published Feb. 19, 2009 under Publication No. WO 2009/021326).

Japanese Abstract of JP 04-224746 published Aug. 14, 1992.

Supplementary European Search Report; EP Appl. No. 08783366.1; Applicant: Garth T. Webb; Date of Completion of Search Report Jun. 10, 2013.

* cited by examiner

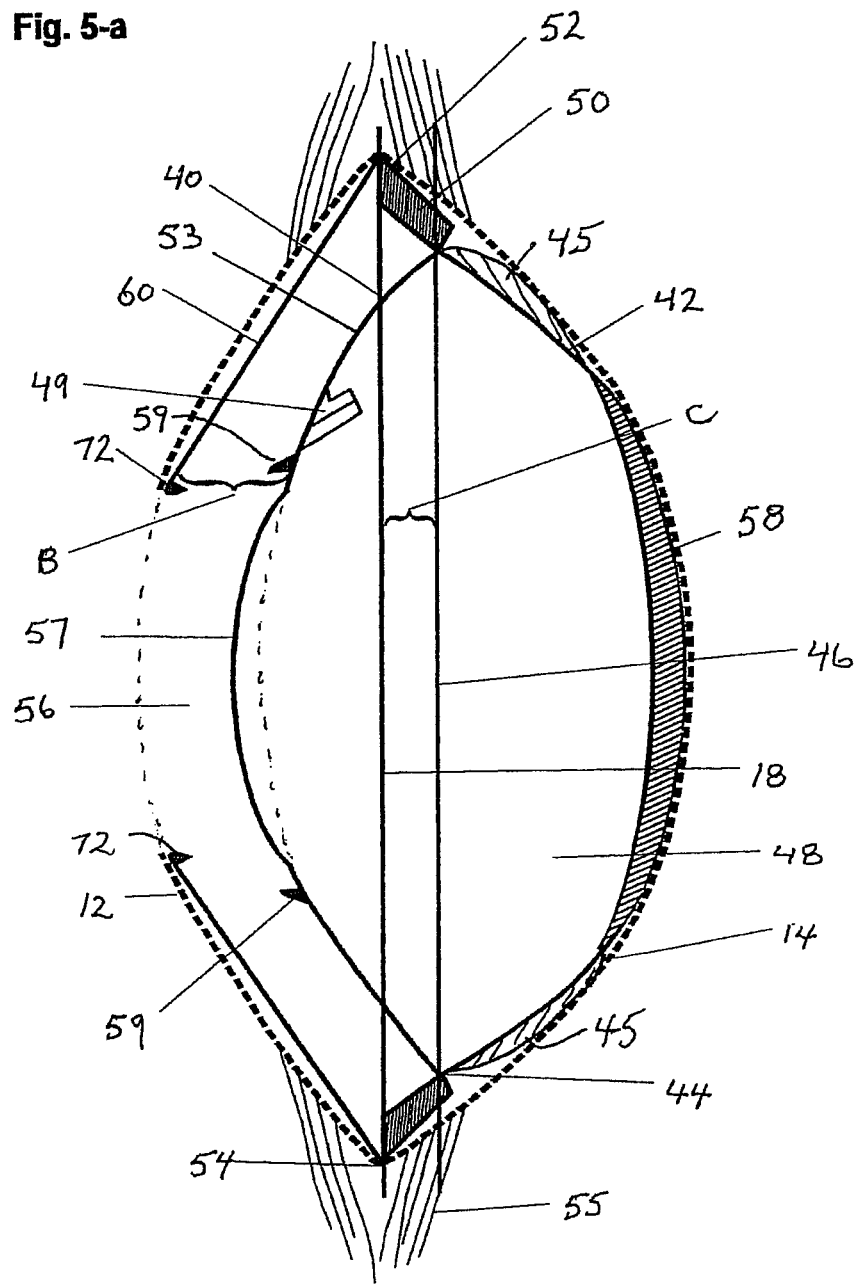
Fig. 5-a

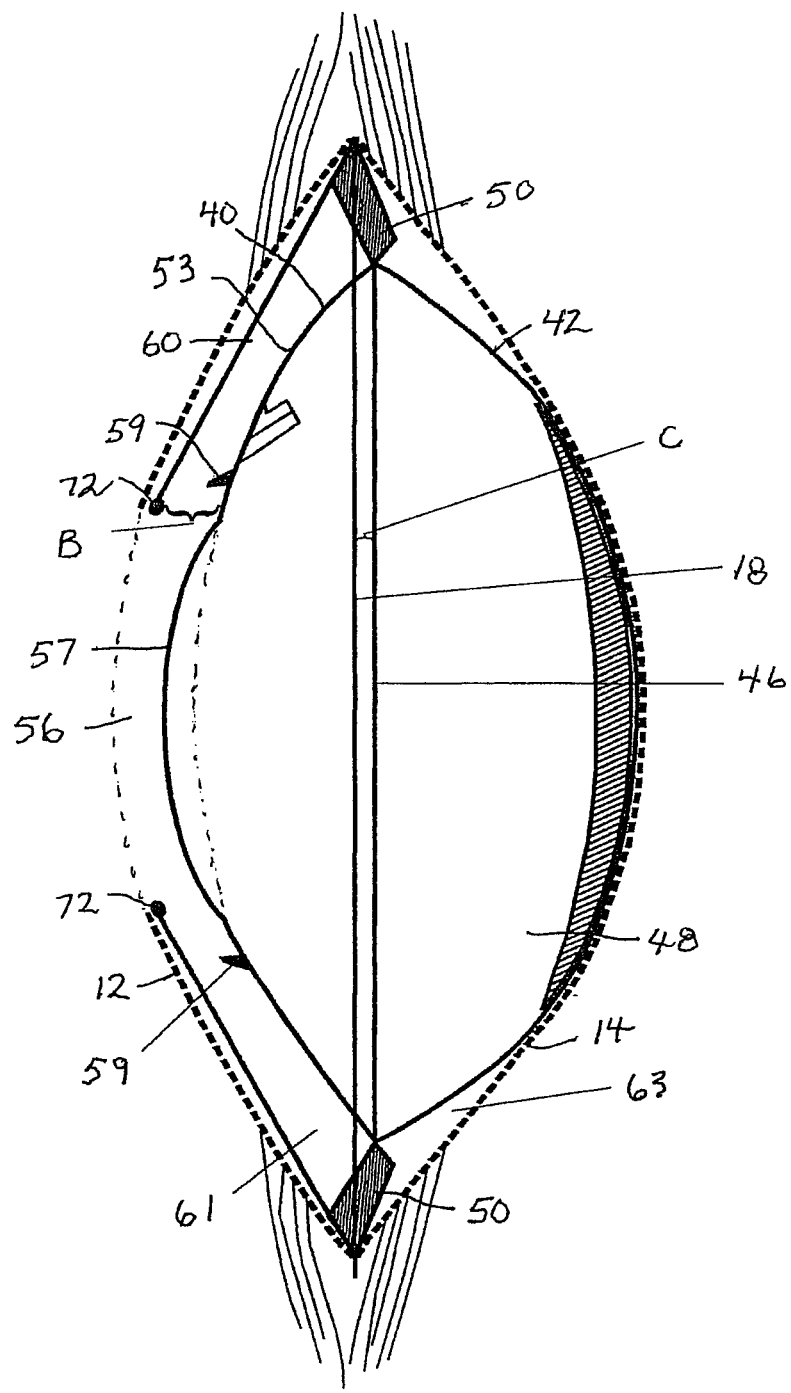
Fig. 5-b

INFLATABLE INTRA OCULAR LENS/LENS RETAINER

REFERENCE TO RELATED APPLICATIONS

The present application claims the benefits, under 35 U.S.C. §119(e), of U.S. Provisional Application Ser. No. 60/955,591 filed Aug. 13, 2007 entitled "INFLATABLE LENS CAPSULE RETAINER" and U.S. Provisional Application Ser. No. 61/051,075 filed May 7, 2008 entitled "INFLATABLE INTRA OCULAR LENS/LENS RETAINER" which are incorporated herein by this reference.

TECHNICAL FIELD

The invention relates to the field of intra-ocular implants.

BACKGROUND

The human crystalline lens is encapsulated by a transparent fibrous envelope called the lens capsule and is suspended behind the pupil by a network of fibrous ligaments called zonules. These zonules run radially along the entire equator of the lens capsule and attach it to the processes of the ciliary body (see FIG. 1). The muscles of the ciliary body pull systematically upon the zonules to compress the contents of the lens capsule, changing the curvature of the crystalline lens, thereby focusing the eye upon different distances within space. This is called accommodation and for young people who have resilient crystalline lenses with little internal resistance, it happens almost instantaneously.

The eye focuses upon distant objects when the ciliary body dilates. The zonules pull upon the equator of the lens capsule causing the opposing walls of the lens capsule to squeeze the crystalline lens, compressing and flattening it into its extended shape. Conversely, when the ciliary body constricts, tension within the zonules is relaxed and elastic forces within the crystalline lens return it to its steeper or distended habitual shape, focusing the eye upon near objects.

The efficiency of the energy translation converting radial traction to intra-capsular compression is expressed by the following equation, provided that the natural geometric shape of the lens capsule is substantially preserved:

Intra Capsular Compression=Zonular Tension(cos $x$+sin $x$−1)−Internal Resistance where angle x is defined by the equatorial plane of the lens capsule and two points, a and b (FIG. 2). Point a may be any point upon the surface of either the anterior or the posterior lens capsule. Point b is the point on the equator of the lens capsule that is geometrically closest to point a (see FIG. 2). For angle x'=30 degrees and angle x"=45 degrees, the efficiency for this energy translation is: 0.360 and 0.414 respectively. These values are consistent within a 15% margin. The most efficient intra-capsular compression possible occurs when angle x is 45 degrees, which is close to the natural geometric shape of the posterior lens capsule. The anterior lens capsule is slightly flatter. Further it is noted that this energy translation may be conveyed even when the central zones of the lens capsule are removed, as tractional force is dispersed distally to the remaining intact regions of the lens capsule, provided that the natural geometric shape of the remaining regions of the lens capsule are substantially preserved.

Extra-capsular lens extraction is a surgical procedure whereby the crystalline lens within the human eye is removed while sparing the peripheral regions of the anterior lens capsule, the posterior lens capsule and the zonules. The central region of the posterior lens capsule is often removed post-operatively, to clear away opaque fibrous material. Conventionally, the extracted crystalline lens is replaced by a synthetic lens which is suspended within a collapsed and gaping lens capsule by means of hooks, wires, springs and the like. The geometric shape of the lens capsule is compromised and the functional relationship between it and the ciliary body is lost, resulting in a complete loss of accommodation. The contents of the vitreous body are precipitously shifted out of normal position leaving the eye vulnerable to a host of post-operative complications, such as vitreous membrane obstructions, retinal detachment, macular trauma, etc.

Attempts to restore the post-operative loss of accommodation may be divided into three categories. The first simply entails the conventional installation of a multi-focal intra-ocular lens implant. These devices create unwanted night-time glare, poor contrast sensitivity and provide very limited near point vision. The second variety, which is more difficult to install, changes the vergence of light with the use of mechanical suspension systems that shift the position of a mono-focal intra-ocular lens forward toward the iris plane in response to ciliary muscle action to focus the eye upon near objects. This is referred to as 'pseudo accommodation'. Apparatus of the "pseudo-accommodative" type are shown in U.S. Pat. No. 6,027,531 Tassignon and United States Patent Application Publication no. 2007/0123981 Tassignon. Damaging wear on the bearing surfaces of the lens capsule remains a long term concern. The third category is referred to as 'accommodative' intra-ocular lenses. These lenses actually change curvature in response to changes of ciliary muscle tone. Recently, an intra-ocular implant which consists of a resilient bi-convex lens and a suspension system made of springs and flexible housing materials, has been introduced to the market place under the trademark CRYSTALENS by Sysonics, Inc. This entire apparatus is introduced into the anterior chamber of the eye and then fitted into the aphakic lens capsule. Material fatigue and again, damaging wear on the bearing surfaces of the lens capsule are long term issues yet to be assessed.

There are complications with each of these devices but collectively, the downside is gross distortion of the geometric shape of the lens capsule, causing vitreous displacement and loss of efficient accommodative facility. There is therefore a need for improvement.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

An inflatable intra ocular retainer for implantation into the intra-capsular space of the lens capsule of an aphakic eye, comprising: i) an inflatable intra ocular retainer body of elastically deformable material, forming a hollow interior chamber, and having an anterior surface and a posterior surface and a central transparent optical zone, said body sized when inflated to bear directly or indirectly against the inner surface of the lens capsule; and ii) means for inflating said retainer body with a liquid.

The invention further provides an inflatable intra ocular lens/lens retainer in the form of a sealed or selectively sealed (i.e. semi-permeable) fluid-filled compartment which is installed within the eye after lens extraction.

According to one aspect, the invention provides for an inflatable intra ocular retainer or a system of inflatable intra ocular retainers which are fitted into the lens capsule or the posterior chamber of an eye after lens extraction, to substantially occupy the space previously held by the crystalline lens to retain and secure the position of delicate intra ocular structures.

According to a further aspect, the invention provides for an inflatable intra ocular retainer or a system of inflatable intra ocular retainers, which are fitted into the lens capsule or the posterior chamber of an eye after lens extraction, to suspend either an integrated or an adjunct intra ocular lens upon the visual axis of the eye.

According to a further aspect, the invention provides for an inflatable intra ocular retainer or a system of inflatable intra ocular retainers, which are fitted into the lens capsule or the posterior chamber of an eye after lens extraction, to press directly or indirectly against residual elements of the lens capsule, substantially restoring its natural geometric shape, and to concurrently press against either an integrated or an adjunct accommodative intra ocular lens system to alter its refractive state in response to changes of ciliary muscle tone.

According to a further aspect, the invention provides for an inflatable intra ocular retainer or a system of inflatable intra ocular retainers, which are fitted into the posterior chamber of an eye after lens extraction and lens capsule removal, to press directly against the ciliary body to change the refractive state of an integrated accommodative lens system in response to changes of the ciliary muscle tone.

According to a further aspect, the invention provides for an inflatable intra ocular retainer or a system of inflatable intra ocular retainers, which are fitted into an aphakic lens capsule or posterior chamber after extra-capsular lens extraction, to press directly or indirectly against the inner surface of at least one of the lens capsule walls, substantially restoring its natural geometric shape, and to concurrently press against a compatible intra-ocular lens implant, or its suspension system, to thereby alter the refractive state of the intra-ocular implant.

According to a further aspect, the invention provides for an inflatable intra ocular retainer with an integrated suspension system, which is fitted into an aphakic lens capsule or posterior chamber after extra-capsular lens extraction, to press directly or indirectly against the inner surface of at least one of the lens capsule walls, substantially restoring its natural geometric shape, and to concurrently press against a compatible intra-ocular lens implant, or its suspension system, to thereby alter the refractive state of the intra-ocular implant.

In addition to the exemplary aspects and embodiments described above, further aspects and embodiments will become apparent by reference to the drawings and by study of the following detailed descriptions.

BRIEF DESCRIPTION OF DRAWINGS

Exemplary embodiments are illustrated in referenced figures of the drawings. It is intended that the embodiments and figures disclosed herein are to be considered illustrative rather than restrictive.

In drawings which illustrate a preferred embodiment of the invention:

FIG. 5-*a* is a vertical cross section of a third embodiment of the invention in distended state.

FIG. 5-*b* is a vertical cross section of the embodiment of the invention shown in FIG. 5-*a* in extended state.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Figure 1:
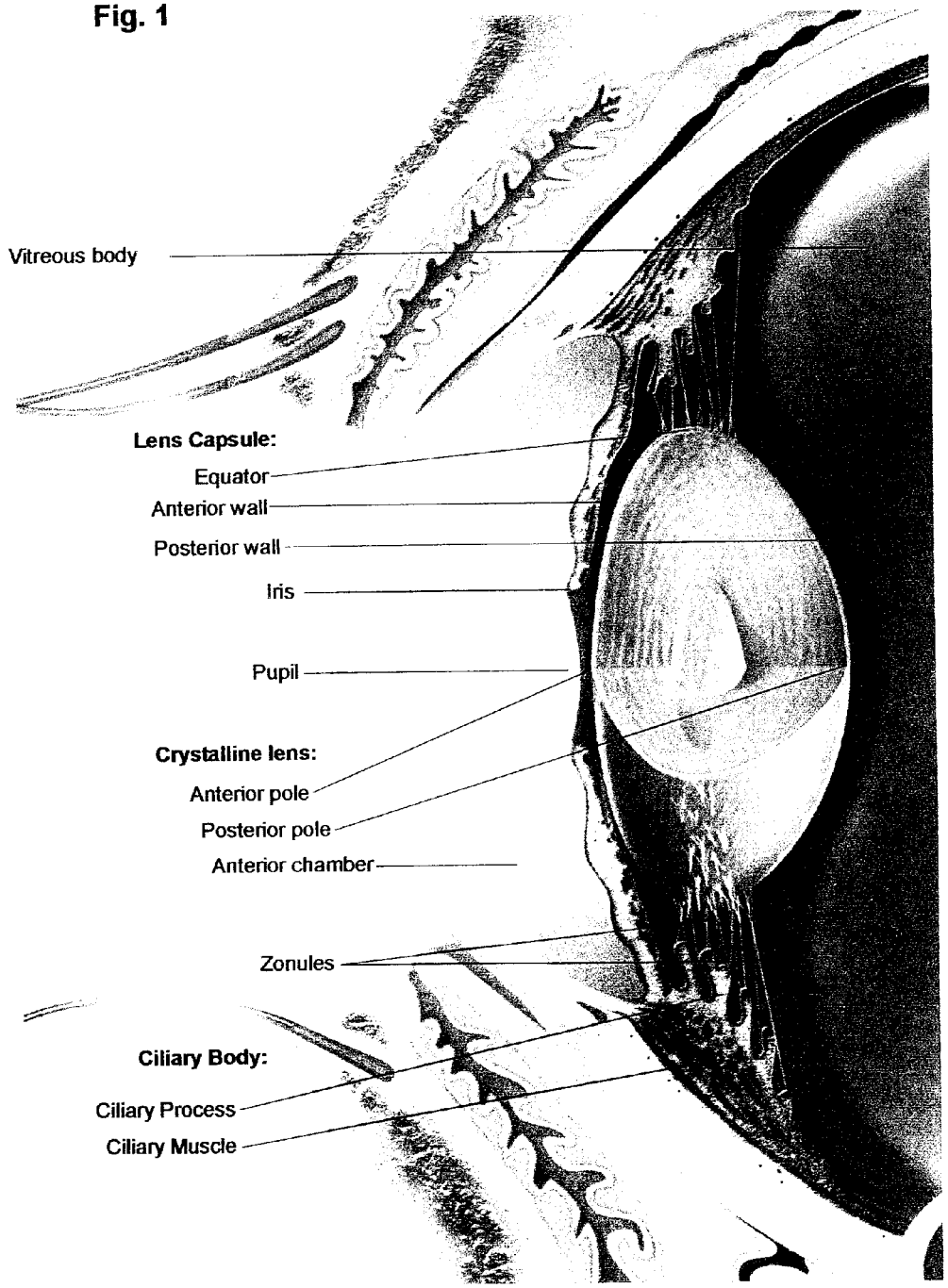
FIG. 1 is a diagram illustrating the components of the related ocular anatomy.

Relevant anatomical features of the human eye are illustrated in FIG. 1 as described above.

Figure 2:
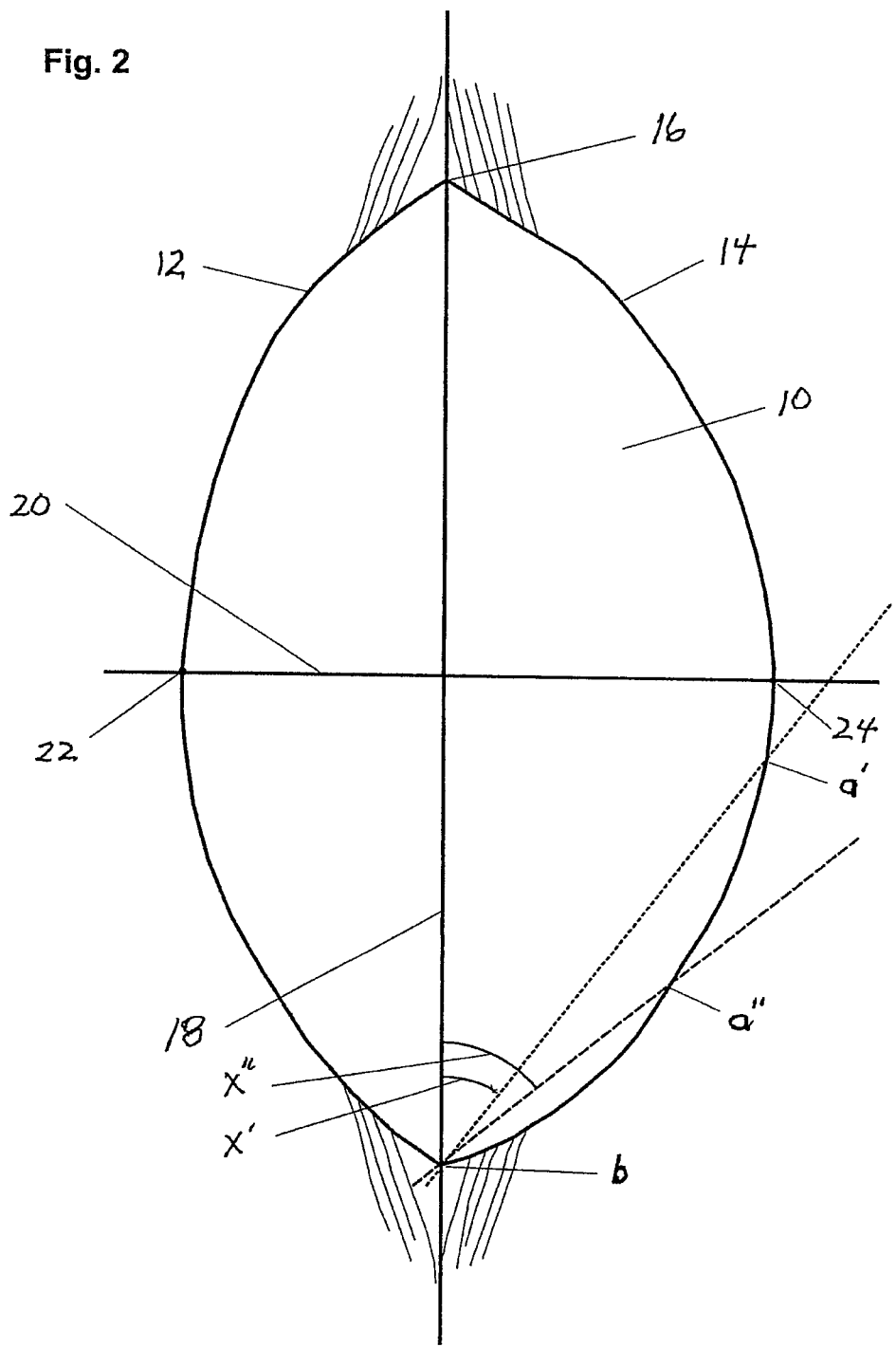
FIG. 2 is a diagram illustrating the components of angle x.

FIG. 2 is a schematic illustration of the human lens capsule. Intra capsular space 10 is defined by the region between anterior lens capsule 12 and posterior lens capsule 14 which join at equator of lens capsule 16. The equator of lens capsule 16 defines the equatorial plane 18 of the lens capsule. Optical axis 20 is the straight line that connects two points, anterior pole 22 and posterior pole 24.

Figure 3:
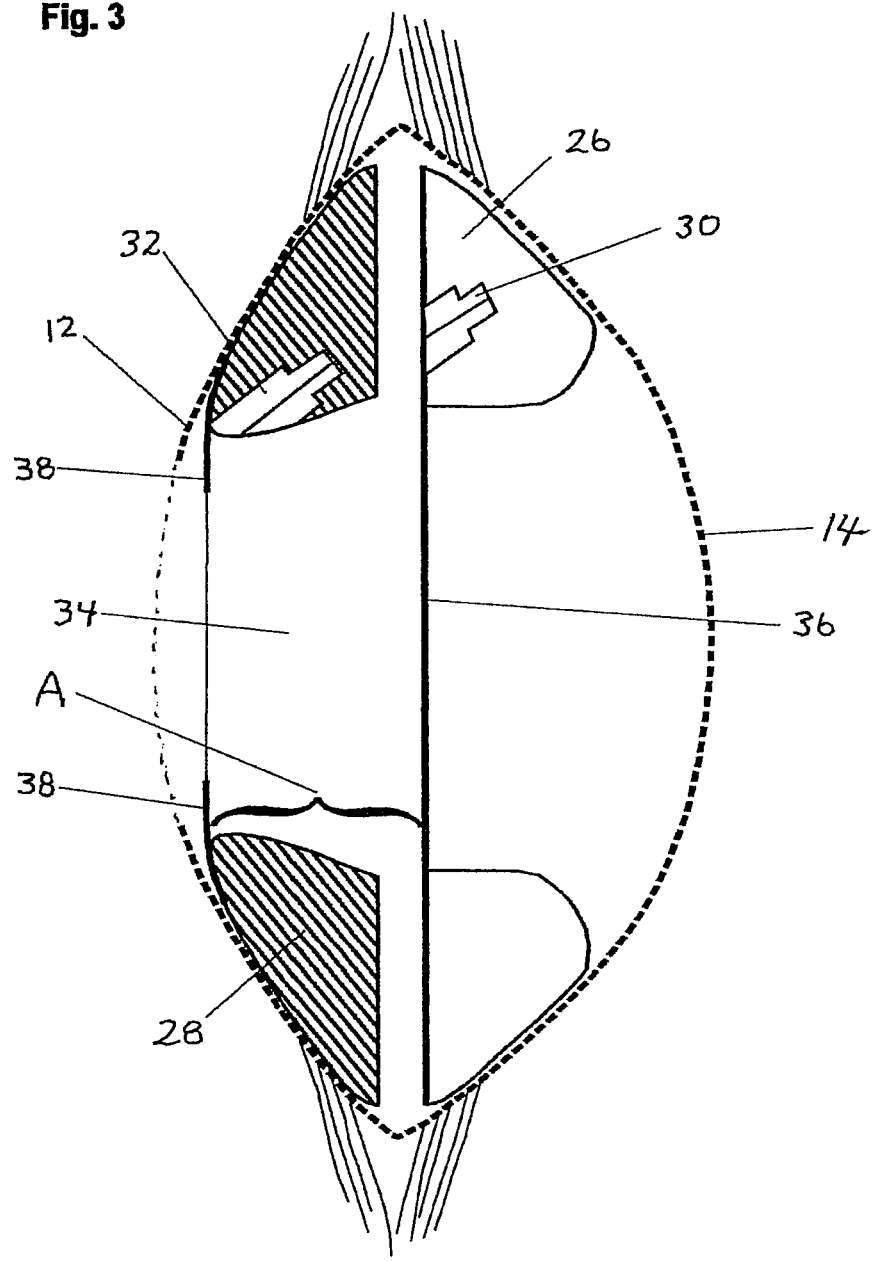
FIG. 3 is a vertical cross section of a first embodiment of the invention.

FIG. 3 illustrates an embodiment of the invention where annular inflatable intra ocular retainer[1] 26 is positioned within the intra-capsular space 10, directly in front of posterior lens capsule 14 and annular inflatable intra ocular retainer[2] 28 is positioned behind anterior lens capsule 12. Liquid is introduced into inflatable intra ocular retainer[1] 26 through filling port[1] 30. The term "liquid" herein refers to both liquids and gas, that is materials in either liquid or gaseous states. Liquid is introduced into inflatable intra ocular retainer[2] 28 through filling port[2] 32. Lens compartment 34 is defined as the space between posterior lens support 36 and anterior lens support 38. Posterior lens support 36 is a diaphragm that stretches across the front surface of inflatable intra ocular retainer[1] 26 and anterior lens support 38 is an annular diaphragm that stretches across the front surface of inflatable intra ocular retainer[2] 28. These 'doughnut' shaped inflatable intra ocular retainers 26, 28 are pressed directly against the mid-peripheral zones of the walls of the lens capsule once a compatible accommodative or a pseudo-accommodative intra-ocular implant is installed. Zonular tension compresses the intra-capsular space and pushes the lens capsule retainers 26, 28 toward each other. The depth A of lens compartment 34 varies as the zonular tension changes, thereby actuating compatible intra-ocular lens implants. This embodiment demonstrates the ability of inflatable intra ocular retainers to re-establish the mechanisms required to activate accommodative intra-ocular lenses while retaining the geometric shape of only the mid-peripheral regions of the lens capsule.

Figure 4:
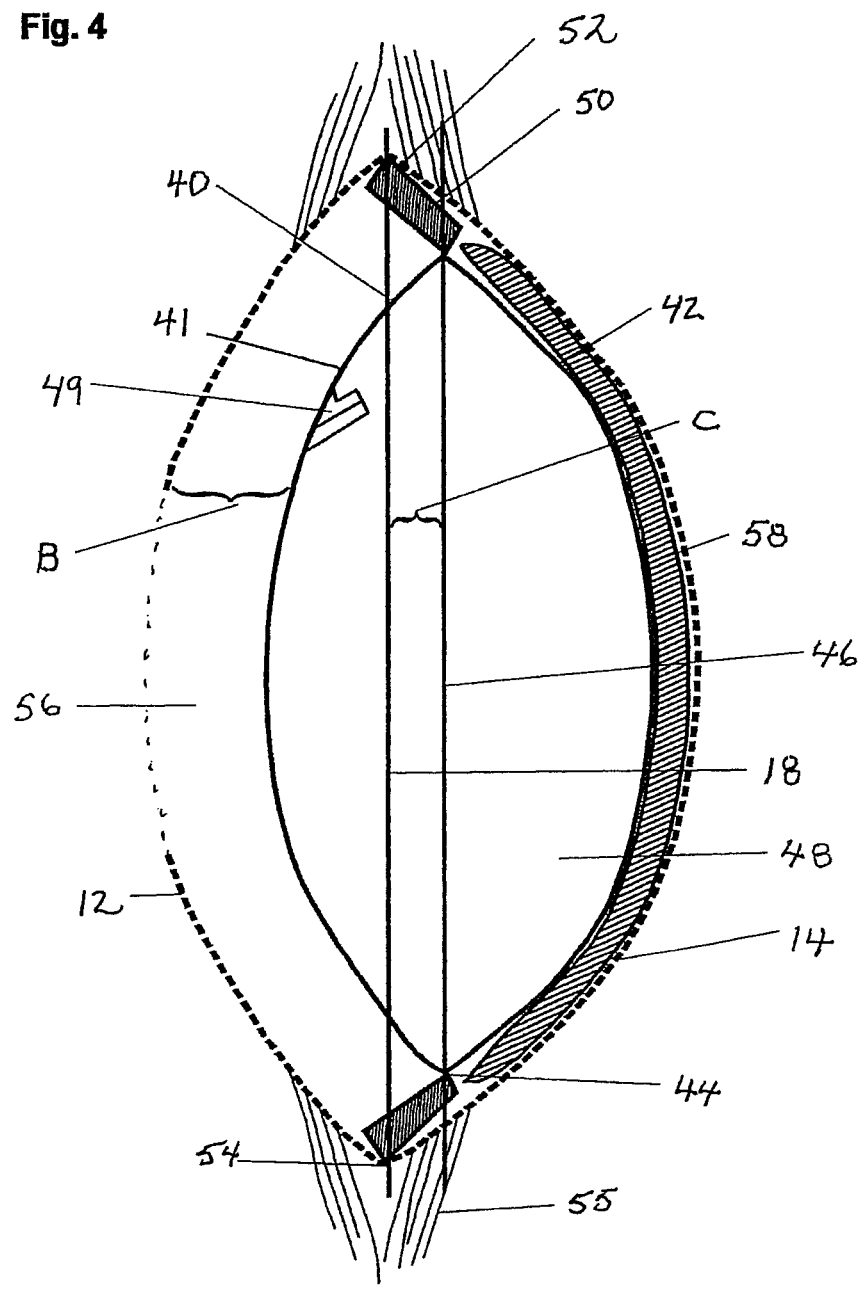
FIG. 4 is a vertical cross section of a second embodiment of the invention.

FIG. 4 illustrates an embodiment of the invention where an inflatable intra ocular retainer 41 is positioned within the intra-capsular space, directly in front of the posterior lens capsule, reestablishing its natural geometric shape. Anterior retainer wall 40 attaches circumferentially to posterior retainer wall 42, at equator 44 of retainer 41. Equator 44 of retainer 41 defines equatorial plane 46 of the retainer 41. The space defined between anterior retainer wall 40 and posterior retainer wall 42 is cushion 48. An integrated suspension system, consisting of a series of armatures 50, is hinged circumferentially around equator 44 of inflatable intra ocular retainer 41. The distal points 52 of armatures 50 fit into the inner surface of the equator 54 of the lens capsule, suspending the inflatable intra ocular retainer 41 centrally along the optical axis. Intra-ocular lens implants may be installed into lens compartment 56 which is the space between anterior lens capsule 12 and anterior retainer wall 40. Elastic forces within compatible ocular lens implants press the inflatable intra ocular retainer against the posterior lens capsule 14, thereby increasing the depth B of lens compartment 56. Conversely, zonular tension from zonules 55 compresses the intra-capsular space and pushes the inflatable lens capsule forward toward the anterior lens capsule 12, reducing the depth B of lens compartment 56 to compress a compatible ocular lens implant. The efficient dynamic between the ciliary body and lens compartment 56 is thus established.

Posterior shield 58 exists as an independent component as shown in FIG. 4 or it may be integrated within posterior retainer wall 42 as shown in FIG. 5-a. The posterior shield 58 is a protective interface which prevents damage to the inner surface of the posterior retainer wall 42 of the retainer in the event of posterior capsular laser oblation. It also provides rigid support to minimize herniation of the inflatable intra ocular retainer through a hole in the central region of the posterior lens capsule 14.

Figure 6:
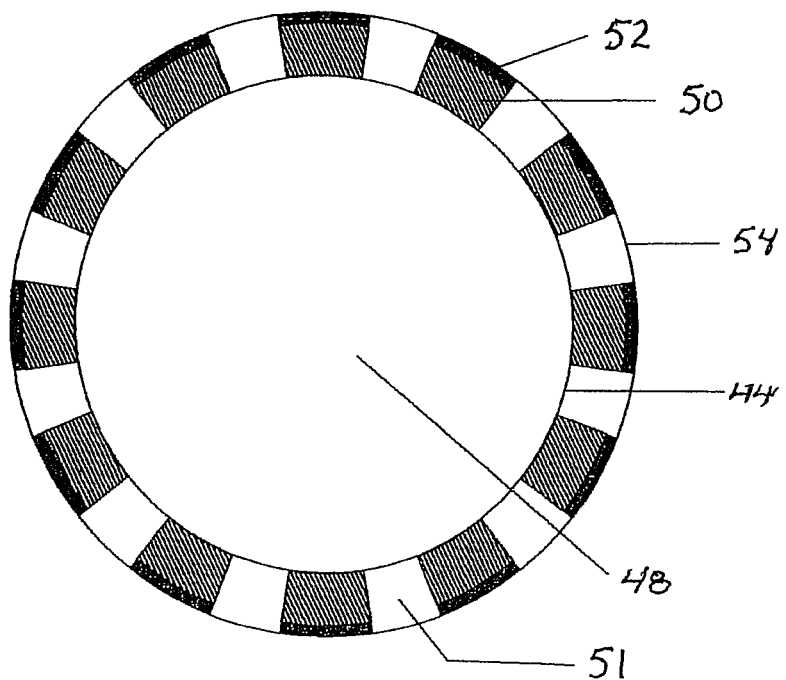
FIG. 6 is a front view of the invention with integrated suspension armatures.

FIG. 5-a and FIG. 5-b illustrate an embodiment of the invention where an inflatable intra ocular retainer 53 is positioned within the intra-capsular space, directly in front of the posterior lens capsule 14, re-establishing its natural geometric shape. An integrated suspension system, consisting of a series of armatures 50 separated by openings or vents 51 (FIG. 6), is hinged circumferentially around equator 44 of retainer 53. Distal points 52 of armature 50 fit into the inner surface of the equator 44 of the lens capsule, suspending the inflatable intra ocular retainer centrally along the optical axis. The tips of the distal points 52 of armatures 50 may be shaped with 'claw-like' projections or 'barbs' that hook onto the anterior lens capsule 12 when it stretches from the 'distended' orientation to the 'extended' orientation. FIG. 6 shows a frontal view of the integrated suspension system. An inflatable doughnut shaped cushion 45 may also be used to position and support retainer 53 within lens capsule 12. Doughnut-shaped cushion 45 can be inflated by laser-activated gas releasing agents (such as collagens or carbamides suspended in the cushion) to position and tighten retainer 53 against the resisting structure.

Figure 7:
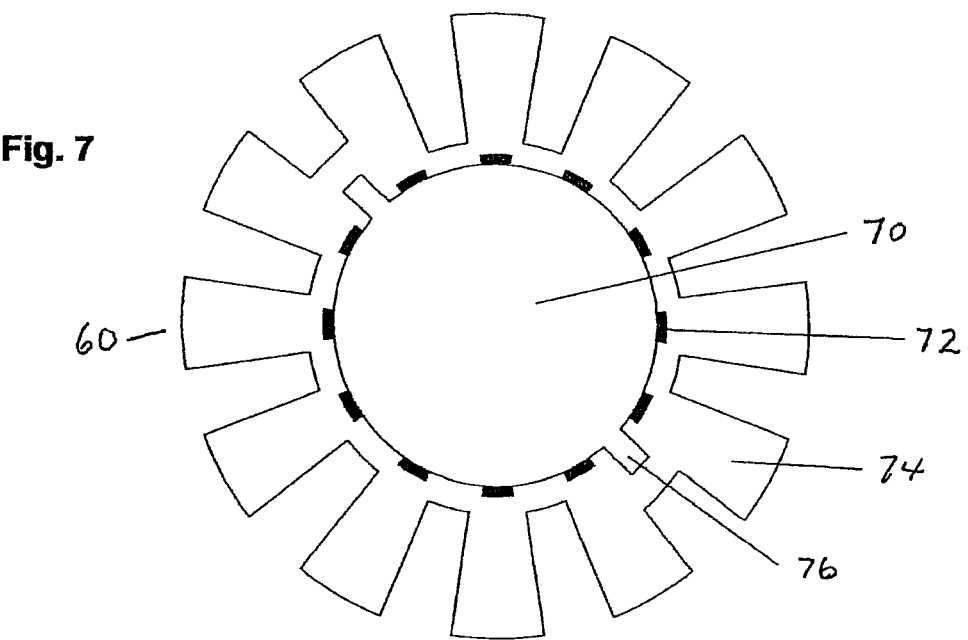
FIG. 7 is a front view of the anterior shield.

The embodiment of the invention on FIG. 5-a and 5-b features a flexible membrane called the anterior shield 60, shown in front view in FIG. 7. The anterior shield 60 serves to protect the anterior lens capsule 12 from the potential of trauma associated with intra-ocular lens installation; however, elements of the anterior shield 60 may be used to assist with the actuation of compatible accommodative intra ocular lenses.

FIG. 7 is a front view of the anterior shield 60. Circular opening 70 may have one or more notches 76 in its perimeter to facilitate the removal of unwanted intra ocular lens implants or to otherwise provide access to the lens compartment 56. Circular opening 70 is circumscribed by a series of claw-like projections called collarets 72. The collaret 72 extends into lens compartment 56 which is the space between the collaret 72 and anterior wall of retainer 40, to hold or grip onto compatible accommodative intra ocular lenses. Anterior radiations 74 are a series of projections of the anterior shield 60 that radiate distally from the collaret 72 and attach to corresponding distal points 52 of armatures 50.

FIG. 5-a is a cross section of the invention in its 'distended' state. Armature 50 is bent forward, displacing the equatorial plane 46 of the cushion 48 away from the equatorial plane 18 of the lens capsule so as to increase equatorial separation C. Simultaneously, the bending forward of armature 50 reduces the tension placed upon anterior radiations 74 (FIG. 7), allowing lens compartment 56 to expand, thereby increasing depth of lens compartment 56. These mechanical movements are synchronized to jointly increase the depth of lens compartment 56, to reduce the compression placed upon compatible accommodative intra-ocular lenses.

Conversely, FIG. 5-b is a cross section the invention in its 'extended' state. Armature 50 is bent backward, displacing the equatorial plane 46 of the cushion 48 toward equatorial plane of lens capsule 18 so as to decrease equatorial separation C. Simultaneously, the extending backward of armature 50 increases the tension placed upon anterior radiations 74, causing lens compartment 56 to compress, thereby decreasing the depth of lens compartment 56. These mechanical movements are synchronized jointly to decrease the depth of lens compartment 56. Thereby, the efficient dynamic between the ciliary body and lens compartment 56 is established for the actuation of compatible intra ocular lens implants.

Cushion 48 may be filled and pressurized with a variety of transparent liquids or gasses once the inflatable posterior lens capsule retainer is positioned within the lens capsule. Fluid is forced into cushion 48 through filling port 49 which is attached to the inner surface of the anterior wall of cushion 49. Filling port 49 is situated in a peripheral region of the cushion 48 so as not to obstruct light entering the eye through the pupil. There are many varieties of one-way valves that may be used within the filling ports 30, 32, 49, 114 (FIG. 9), and 142 (FIG. 11A) to retain the liquid cushions of the five embodiments of the invention shown. Laser energy may be used to weld and seal these filling ports shut.

Liquids of various viscosities may be selected to fill the retainer 26, 28, 41, 53. Highly hydrophilic polymers, glycerin or concentrated solutions of visco-elastics, polysaccarides, and cellulose may be used to eliminate the need for the one-way valve, or to improve its efficiency. Osmotic agents such as glycerin, dissolved proteins, and electrolytes may be placed inside the inflatable retainer to induce osmotic pressure that may be used to fill the inflatable retainer with water from the ambient aqueous humor, eliminating the need for an attached hydraulic filling apparatus and filling port altogether. Structural elements of the inflatable retainer in that case are made of a semi-permeable material to facilitate the flow of water into the inflatable retainer. Hydraulic pressure, induced upon an inflatable intra ocular retainer by the compression of the ciliary muscles, may be used to create enough internal pressure (tugor) to reverse the flow of water molecules out of the retainer and back into the aqueous humor (reverse osmosis) as needed. This feature may be used to maintain a dynamic balance of pressure within the inflatable intra ocular retainer during the act of accommodation. A 'distended' state would allow water to enter into the retainer and an 'extended' state would express water out of the retainer and back into the eye. Osmotic agents such as these may be used either with or without the use of an attached hydraulic filling apparatus and filling port as they may be introduced and sealed within the inflatable intra ocular lens/lens retainer during the manufacturing process. In its simplest form, the inflatable intra ocular lens/lens retainer is a sealed or selectively sealed (i.e. semi-permeable) liquid filled compartment, preferably incorporating the accommodative features shown in FIGS. 8 and 11, which is installed within the eye after lens extraction.

Properties of semi-permeable barriers may be selected so as to regulate the internal pressure of an inflatable retainer and to allow it to expand and compensate for growth, trauma or other events that could alter the volume of the eye over time. Laser energy may be used to irradiate the semi-permeable barrier or other adjacent membranes to modify the osmotic balance in accordance to the needs of each individual eye. Lasers may be used to tighten cross-linkages of the molecular structure of permeable barriers or to create holes within water-tight membranes or to weld laser absorbent materials to laser transparent materials. All of these mechanisms may be used to alter the osmotic balance within the eye. An expandable water absorptive pad made of cellulose or other optically transparent materials could be used as an alternative to hyperosmotic liquids in order to inflate the retainer. In this event, a simple open passage, through any wall of the inflatable lens/lens retainer, permits the flow of ambient intra ocular fluid into the retainer to expand the water absorptive pad. Or the retainer may have multiple orifices, such as a net-like porous structure, to permit the flow of fluid to the absorptive pad which fills and inflates the retainer by imbibition pressure. The imbibition pressure created thus expands the inflatable lens/lens retainer. Preferably, the expandable water absorptive pad should be shaped to match the shape of the natural lens capsule.

An optional feature of the invention is optical interface 57. Optical interface 57 is the central area of anterior retainer wall 40. Optical interface 57 may be filled with liquid from within cushion 48 or with transparent plastic material. Its function is to provide ancillary refractive properties, such as myopic, hyperopic and astigmatic corrections, with compatible intra ocular lens types.

Another optional feature of the invention is the provision of a series of claw-like projections called the optic-perimeter 59. These projections arise from the outer surface of the anterior wall of the retainer and run circumferentially around optical interface 57 to secure the positioning of compatible intra-ocular lens types.

The flow of fresh aqueous humor from the anterior chamber of the eye into lens compartment 56, anterior compartment 61, and posterior compartment 63, is provided by channels (not shown) that run between the projections of collarets 72 and armatures 50. Aqueous humor moves freely back and forth throughout these inter-connected compartments as the lens capsule responds to the changes in tone of the ciliary muscle. Aqueous humor ventilation within the lens capsule is necessary for a number of reasons, but it is especially important to allow the unrestricted movement of delicate structures required to optimize the accommodative facility within certain types of accommodative intra-ocular implants. Additionally, aqueous humor ventilation provides a continuous supply of protective agents such as macrophages to address potential microbial contamination.

The components of the inflatable intra ocular retainer are preferably constructed from optically transparent materials; however, opaque interfaces may be used to reduce distortions, unwanted glare and to limit pupil size. The optical surfaces may include anti-reflective coatings to reduce glare sources and ultra violet, violet and blue absorptive substances to protect delicate internal structures of the eye. The lens capsule retainer 26, 28, 41, 53 may be manufactured from very low density polyethylene and copolymers of polyethylene, polyurethane and copolymers of polyurethane, collagen and copolymer complexes of collagen, such as Collamer™, hydrophylic acrylics or elastomers. These materials may be infused or lined with phospho-lipid agents for improved biocompatibility. The pressure within the lens capsule retainer can be from ambient/atmospheric to 100 psi. Instead of liquid, gasses can be used for inflation, such as gasses which are relatively inert, physiologically compatible and preferably of large molecular weight, such as the ones used for reparative retinal surgery, available from Alcon Laboratories Inc under the trademark Ispan C3F8 for medical grade perflurocarbon gas and Ispan SG6 for medical grade sulfurhexafloride gas. The lens capsule retainer can be manufactured by a plastic injection mold process, split mold process, heat welding or laser welding.

Inflatable intra ocular retainers may be introduced into the eye through a tubule fitted through a small incision, as they may be rolled up upon themselves into small compartments and then inflated once positioned within the intra-capsular space. Intra-ocular implants may then be safely installed within the eye and then easily removed if required. Inflatable intra ocular retainers substantially restore the natural geometric shape of the lens capsule providing for the efficient translation of radial traction to intra-capsular compression to reestablish accommodation while holding the vitreous body in its normal state.

Figure 8:
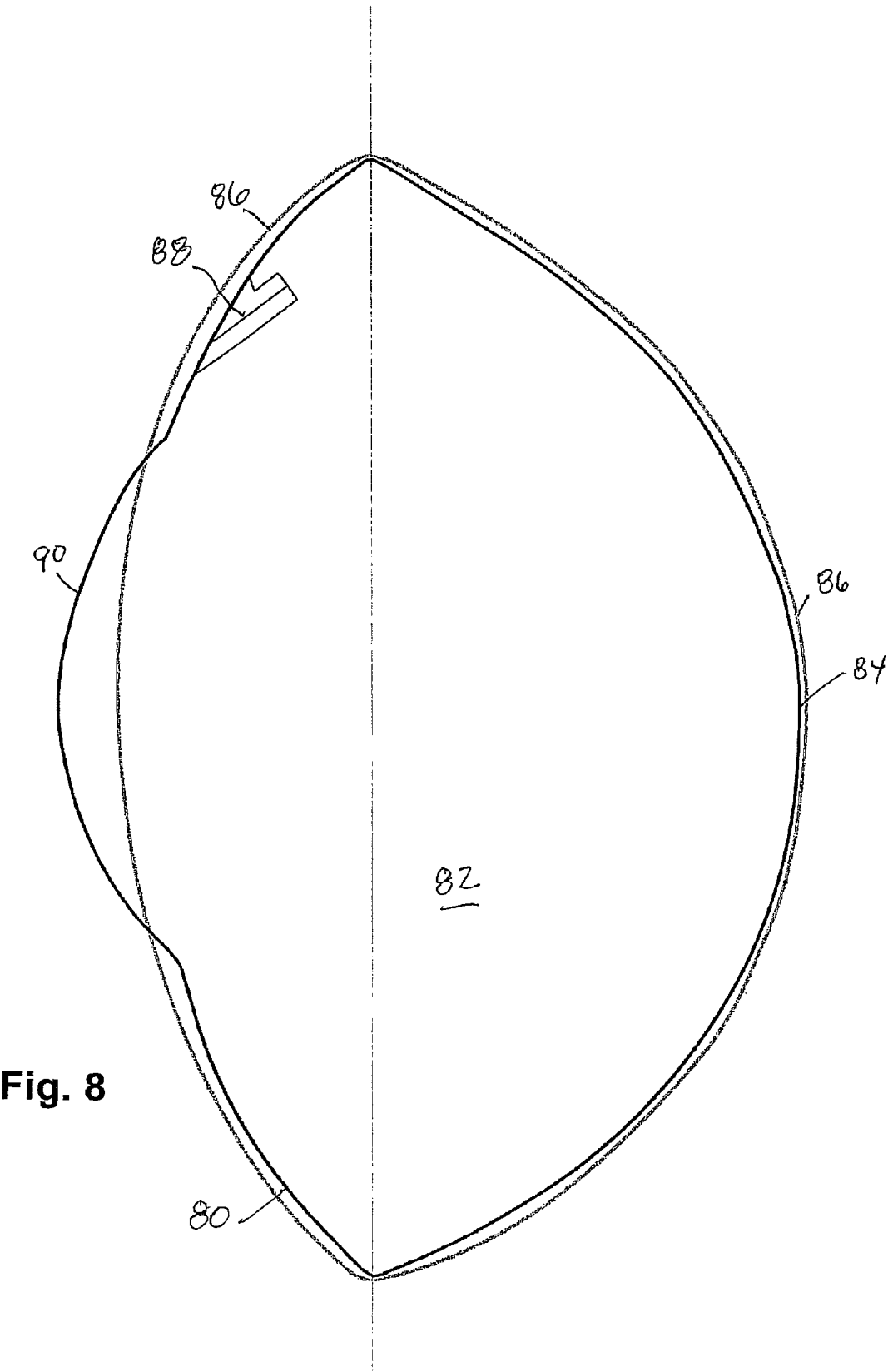
FIG. 8 is a vertical cross section of a fourth embodiment of the invention in which the retainer can act as its own lens.

FIG. 8 illustrates by way of a vertical cross section, a fourth embodiment of the invention in which the retainer 80 can act as its own lens. Retainer 80 is constructed of an elastic material, the interior 82 of which is filled through port 88 with a liquid of a higher index of refraction than water, such as glycerin or silicone oil (from Adatomed Corp. of Germany) or silicone gel. The curvature of the posterior surface, posterior optical interface 84 changes in response to ciliary muscle action. In this case, when the ciliary muscle relaxes, the lens capsule 86 distends and allows the elastic retainer 80 to also distend, resulting in an increase of curvature of the walls of the retainer, particularly the posterior wall 48 and also possibly the anterior optical interface 90. The liquid medium, such as silicone oil, immediately flows to fill the vacant space within the cushion, creating an increase of refractive power. The eye is thus focused for near objects. Conversely, when the ciliary muscle constricts, the lens capsule 86 extends. The walls of the inflatable retainer 80 are compressed and the curvature of its walls are reduced, particularly the posterior wall 84. The refractive power of this optical interface is reduced and the eye is focused upon distant objects. Thus, for this embodiment, the retainer 80 itself is used to create the change of refraction in response to ciliary muscle action. It may be used in conjunction with any other intra-ocular lens or lens system to focus the light upon the retina as required.

It is possible to integrate certain types of accommodative intra-ocular lens directly into the elements of an inflatable intra ocular retainer and then inflate the cushion as the last step in the installation process. However, the fundamental principles of the invention would remain unchanged. A particularly useful type of accommodative intra ocular lens is the pneumatic lens which is the subject of this same Applicant's co-pending U.S. provisional patent application entitled PNEUMATIC INTRA-OCULAR LENS Ser. No. 60/955,619 filed Aug. 13, 2007, and which is incorporated herein by reference.

Figure 9:
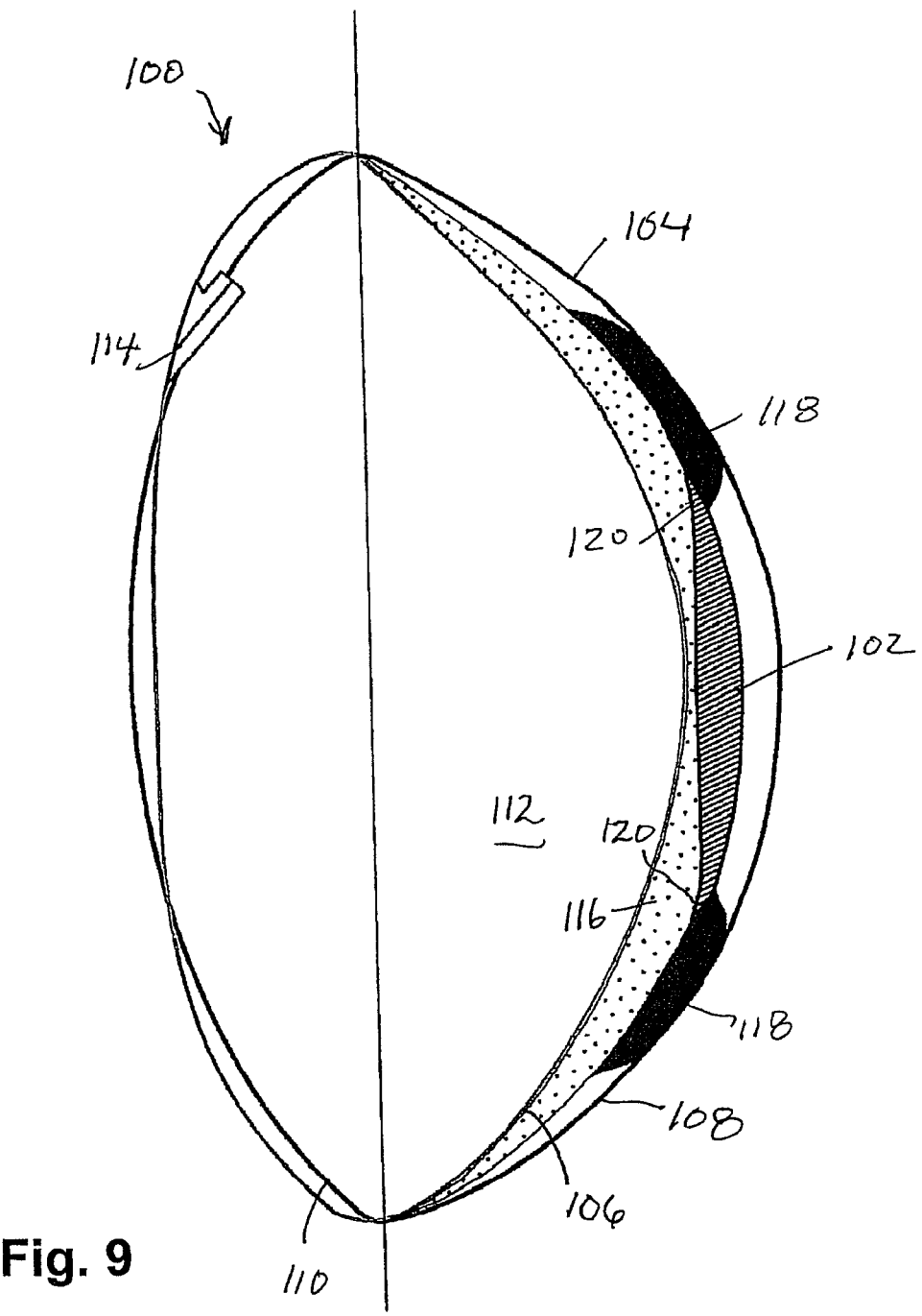
FIG. 9 is a vertical cross-section of a combined inflatable intra ocular retainer and pneumatic lens.
Figure 10:
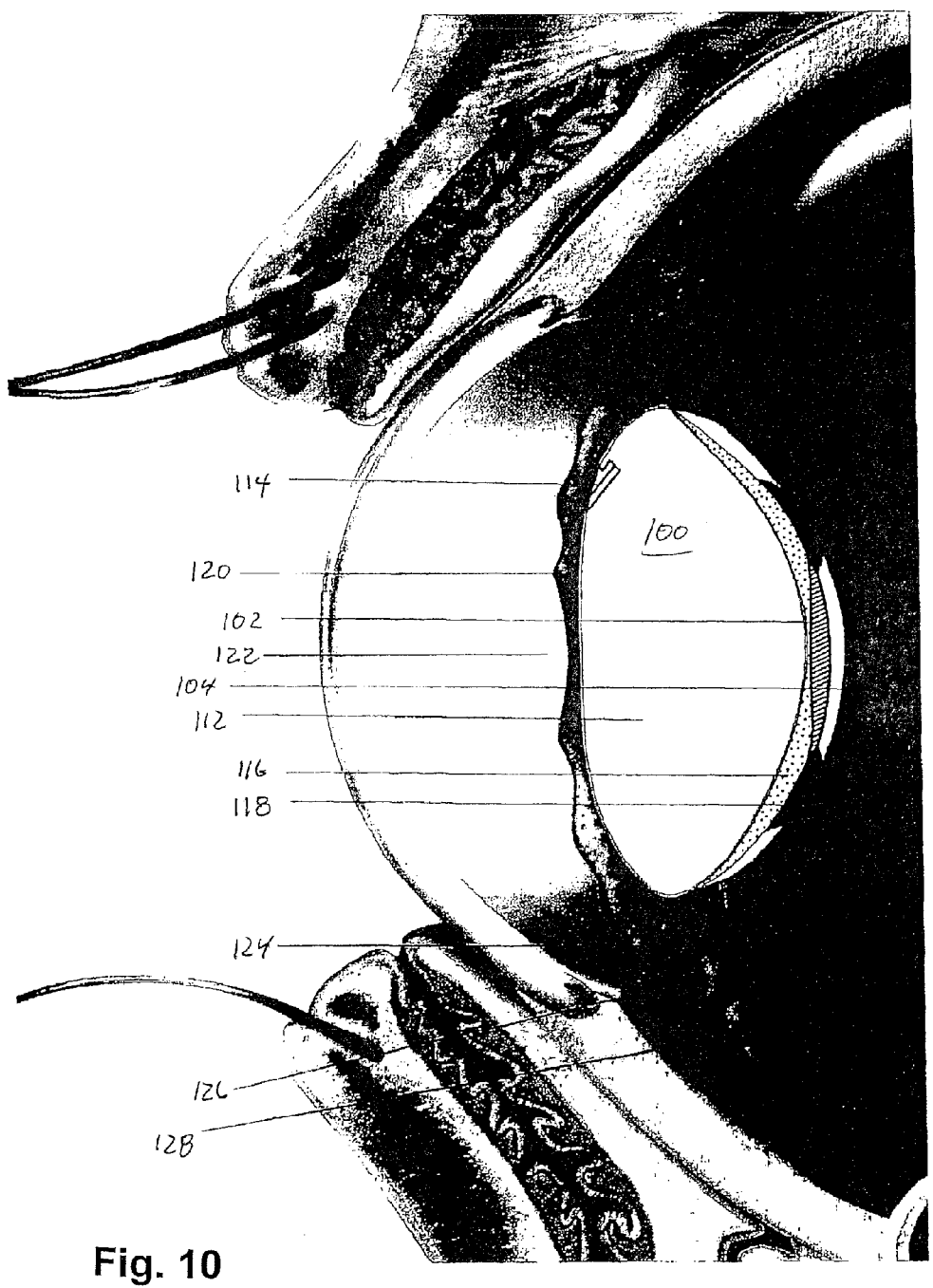
FIG. 10 is a vertical cross-section of the combined inflatable intra ocular retainer and pneumatic lens shown in FIG. 9 in place implanted in a human eye.

The present invention may thus combine an Inflatable Lens Capsule Retainer as disclosed herein with a pneumatic lens as disclosed in U.S. provisional patent application No. 60/955, 619. FIG. 9 is a vertical cross-section of the combined inflatable intra ocular retainer and pneumatic lens 100. FIG. 10 is a vertical cross-section of the combined inflatable intra ocular retainer and pneumatic lens shown in FIG. 9 in place implanted in a human eye. Combined inflatable intra ocular retainer and pneumatic lens 100 has a flexible, supple pneumatic lens 102 as described above located within inflatable intra ocular retainer 104, between an interior anterior retainer wall 106 and exterior anterior retainer wall 108. The space defined between interior anterior retainer wall 106 and posterior retainer wall 110 is cushion 112 which is filled with a liquid, such as an aqueous, water-based filler or glycerine, introduced into cushion 112 through filling port 114. Pneumatic lens 102 is supported by posterior shield 116 and by an inflatable doughnut shaped cushion 118 which extends over the edges 120 of the lens 102. Doughnut-shaped cushion 118 can be inflated by laser-activated gas releasing agents to position and tighten lens 102 and retainer 104 against the resisting structure. The posterior shield 116 is a protective interface which prevents damage to the inner surface of the posterior retainer wall 104 and to lens 102.

With reference to FIG. 10, the human eye has iris 120, pupil 122, zonules 124, ciliary process 126 and ciliary muscles 128. The surgeon may remove the anterior wall of the lens capsule and the combined inflatable intra ocular retainer 100 may be positioned within the intra-capsular space, directly in front of the posterior lens capsule. Or the surgeon may leave the anterior wall of the lens capsule in place and the combined inflatable intra ocular retainer 100 may be positioned between the collapsed anterior wall of the lens capsule and the iris. Or the surgeon may remove the entire lens capsule altogether and place the inflatable intra ocular retainer behind the iris so as to allow the constriction of the ciliary muscle to compress the optical elements of the inflatable intra ocular retainer to focus the eye upon near objects and to conversely release the pressure upon the optical elements to focus the eye upon distant objects.

Both the pneumatic lens described above and the inflatable intra-capsular retainer can be inflated by laser-activated gas-releasing agents which either release gas into the interior of the pneumatic lens or inflatable intra-capsular retainer or into a separate expandable compartment contained within the pneumatic lens described or the inflatable intra-capsular retainer. The inclusion of gas releasing, laser absorptive materials within the hollow interior of the pneumatic lens or retainer may be used to alter the refractive power of the lenses. By irradiating materials within the lens as described above with laser energy to release carbon dioxide, nitrogen and other heavier gasses within the pneumatic lens or retainer, its curvature can be altered or corrected. For example if the eye surgeon determines that a correction to the curvature of the lens is required after insertion, pulsed laser radiation could be directed to release discrete volumes of gas to alter the curvature of at least one surface of the pneumatic intra-ocular lens, allowing the surgeon or clinical refractionist to alter the curvature of the lens surfaces, correct the 'end-point of refraction' of the eye or reshape the optical surface of the collagen interface at the same time as it releases gasses. These adjustments could be performed at the time of surgery or at any future date as needed after the lens or retainer is implanted.

Figure 11A:
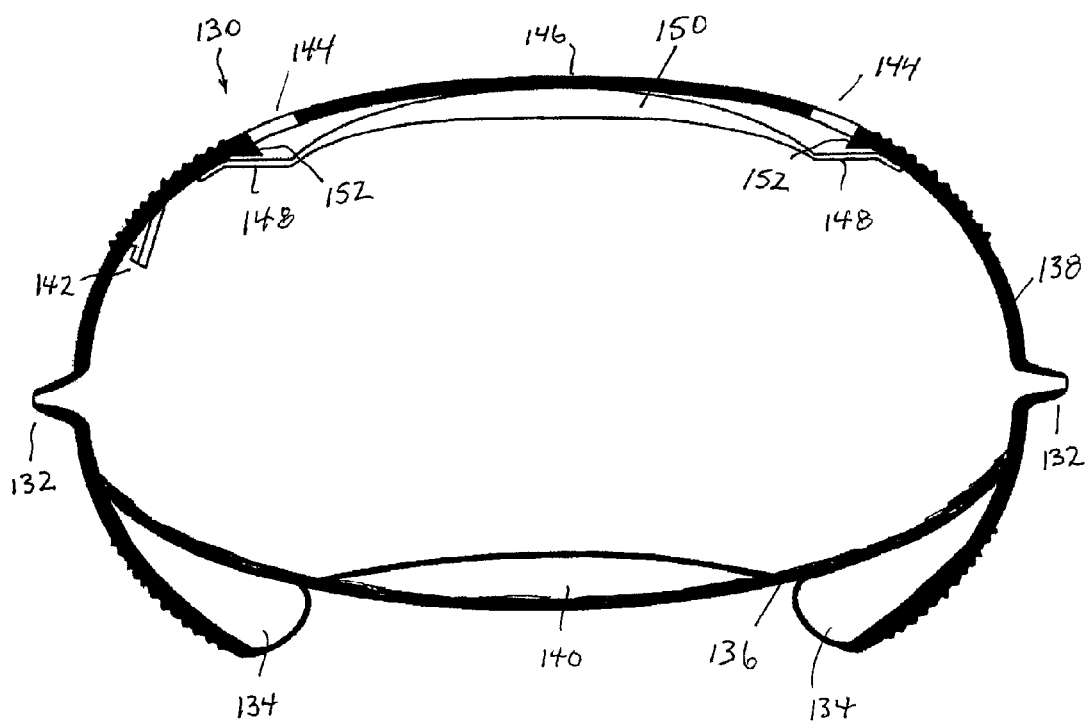
FIG. 11A is a vertical cross section of a fifth embodiment of the invention in which retainer acts as its own lens in its 'distended' state.

FIG. 11A illustrates by way of a vertical cross section, a fifth embodiment of the invention in which retainer 130 acts as its own lens and is shown in its 'extended' state.

Figure 11B:
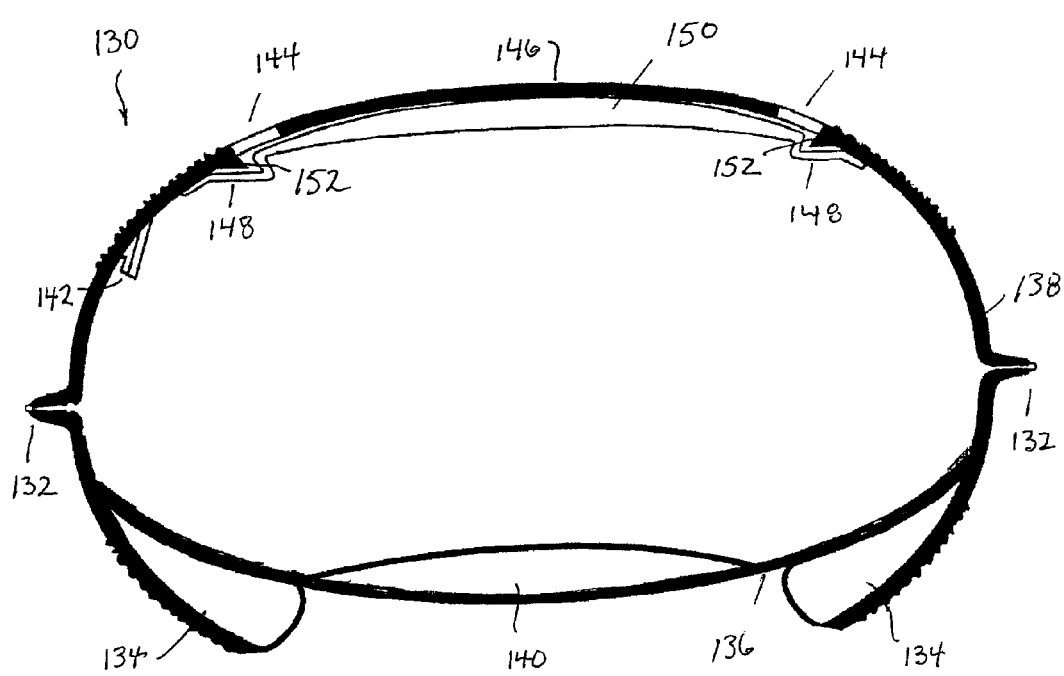
FIG. 11B is a vertical cross section, of the embodiment of the invention shown in FIG. 11*a* in its 'extended' state.
Figure 11C:
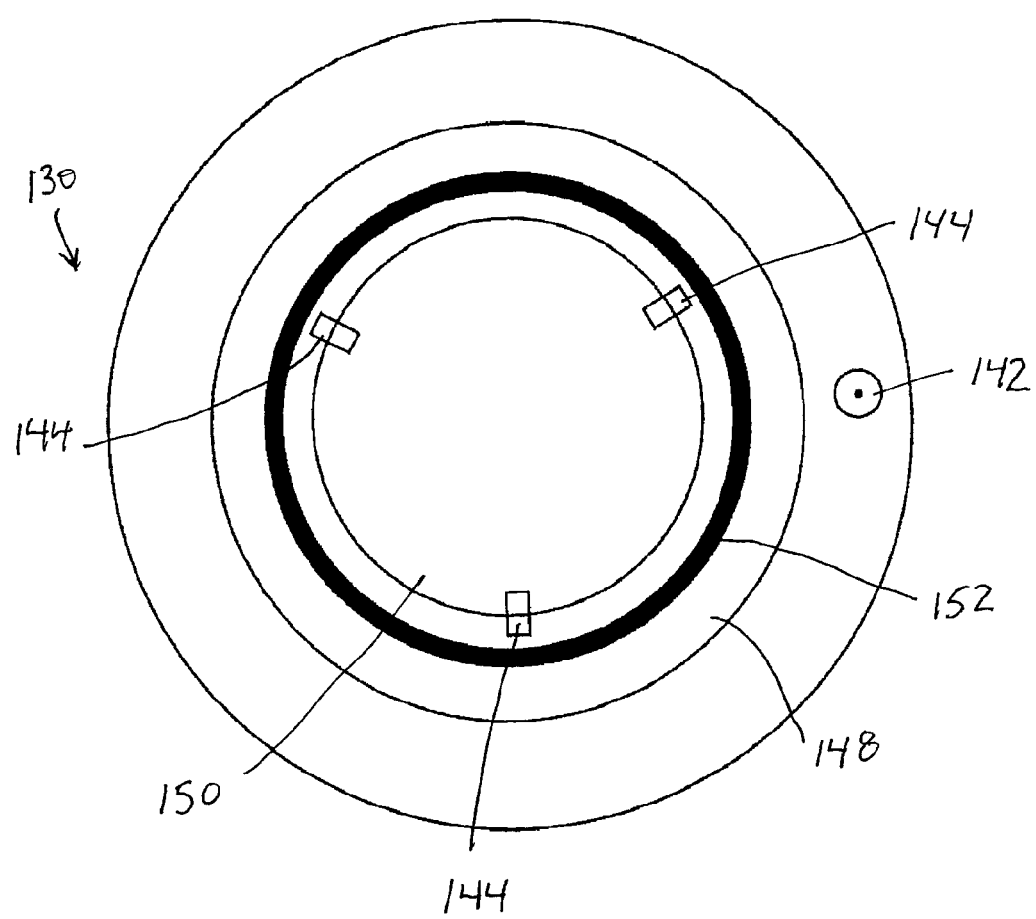
FIG. 11C is a front view of the anterior hemisphere of the embodiment shown in FIG. 11A.

FIG. 11B is a cross section of retainer 130 shown in its 'distended' state. Retainer 130 is a 'clam shell' shaped structure consisting of two hemispheres which are attached or welded together at their equator to create expandable billow 132 that allows the retainer to expand to fit the size of the lens capsule. Expandable billow 132 fits into the equator of the lens capsule.

The peripheral regions of the external surfaces of the two hemispheres 136, 138 may be corrugated or roughened to provide frictional attachment to the lens capsule. These corrugations run circumferentially around the central optical zone of the inflatable retainer and press against the posterior lens capsule to prevent the migration of epithelial cells and inflammatory debris which may opacify the central region of the posterior lens capsule. The inflatable retainer may be infused with biocidal agents to further reduce the chance of epithelial cell migration. Alternatively, the posterior surface of doughnut shaped cushion 134 may be corrugated as shown on FIGS. 11A and 11B. Posterior hemisphere 136 may include posterior shield 140 as shown. Anterior hemisphere 138 houses filling valve 142 which is used to fill the interior of retainer 130 with a liquid of a higher refractive index than aqueous humor such as glycerin or silicone oil. The anterior surface of the anterior hemisphere has several vents 144 which run along the perimeter of optical shield 146. Optical shield 146 may be shaped to provide rigid support and optical resolution as required. The posterior surface of the anterior hemisphere is attached circumferentially to suspension diaphragm 148. Suspension diaphragm 148 is attached circumferentially to resilient optical interface 150. Vents 144 allow aqueous humor to flow within the space between resilient optical interface 150 and optical shield 146. A protrusion extending from the posterior surface of the anterior hemisphere called spur 152 prevents suspension diaphragm 148 from extruding through vents 144 when aqueous humor is exiting.

Resilient optical interface 150 is preferably a convex lens shape which may be shaped with spherical, elliptical or aspheric surfaces to optimize the optical quality of its refractive properties as its curvature varies. Its front surface is formed with a predetermined curvature which is steeper than the curvature of the posterior surface of optical shield 146. The apex of resilient optical interface 150 may be welded or otherwise attached to the posterior surface of optical shield 146 to secure the position of the optical system along the visual axis of the eye.

The refractive index of resilient optical interface 150 would be best matched to the refractive index of the liquid that is used to fill the retainer, such as glycerin, so as to minimize reflections, optical distortions and the appearance of grooves cut within its inner surface. These grooves may be used to translate a smooth transition from a steep curvature to a flatter curvature and vice versa during the process of accommodation.

In operation, resilient optical interface 150 is pressed against optical shield 146 by the compression induced by the extension of the ciliary muscles via the zonules, thereby flattening its curvature. The eye is thus focused upon distant objects. When the ciliary body constricts and tension in the zonules relaxed, elastic properties of the resilient optical interface cause it to return to its original steeper shape, focusing the eye upon near objects.

The refractive power of retainer 130 may be easily predetermined as would its accommodative capacity owing to the interaction between resilient optical interface 150 and optical shield 146.

Doughnut shaped cushion 134 may be filled with osmotic agents used to create an osmotic gradient to press the inflatable retainer against the posterior lens capsule without inducing any refractive index change of the optical elements of the system. For this embodiment of the invention, the osmotic pressure must be great enough to press resilient optical interface 150 against optical shield 146 for optimal performance.

Figure 11D:
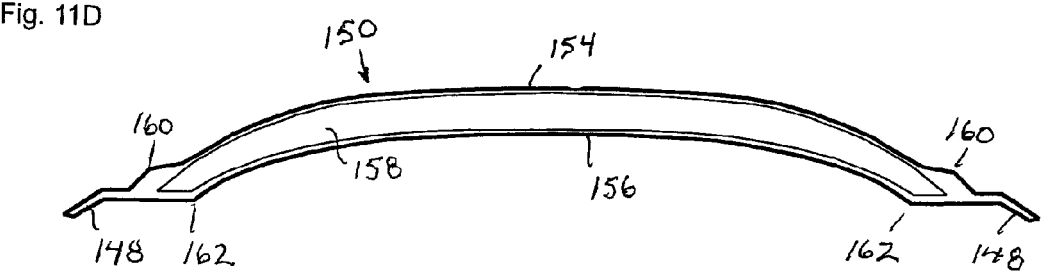
FIG. 11D is a vertical cross section of a resilient optical interface shown in FIG. 11A.

FIG. 11D is a cross section of an embodiment of resilient optical interface 150. In this embodiment, resilient optical interface 150 is actually a fluid filled inflatable lens/lens retainer itself. It consists of anterior membrane 154, posterior membrane 156, and optical spring 158. In this preferred embodiment, anterior membrane 154 is circumscribed by anterior billow 160 and posterior membrane 156 is circumscribed by posterior billow 162. These billows are attached circumferentially to create suspension diaphragm 148 which is attached to the inner wall of the inflatable lens/lens retainer. The space between anterior membrane 154 and posterior membrane 156 may be filled with gas or any transparent liquid as required and then sealed.

Optical spring 158 may be constructed from a wide variety of resilient or rigid optically transparent materials such as silicone rubber, elastomers and acrylics. Preferably, its anterior surface is shaped with a steeper curvature than the posterior surface of optical shield 146 so that it may flatten when the eye is in its 'extended' state, focusing the eye upon distant objects. Elastic forces within optical spring 158 allow it to return to its steeper shape, focusing the eye upon near objects when the eye is in its 'distended' state.

Figure 11E:
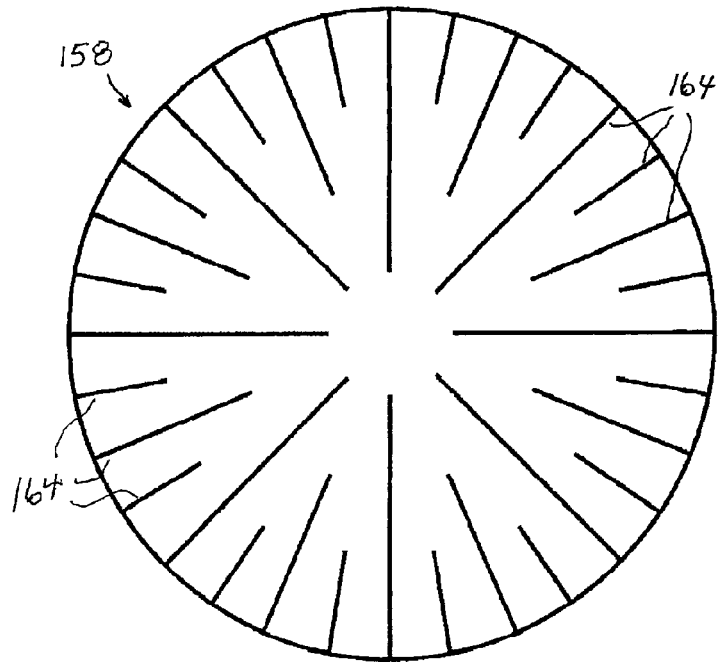
FIG. 11E is a front view of the optical spring for the resilient optical interface shown in FIG. 11D.

FIG. 11E is a front view of optical spring 158. The radial pattern shown within circular optical spring 158 is actually a series of slits 164 which penetrate through the entire thickness of optical spring 158 allowing it to change curvature evenly without the resistance and distortions normally encountered when trying to flatten a hemispherical shell. The liquid, preferably glycerin or silicone oil, allows the surfaces of optical spring 158 to slide almost friction free across the inner surfaces of resilient optical interface 150 as it flattens and steepens in response to the ciliary muscle. It operates much like a parasol as it protrudes back and forth into the space between the two billows. The refractive index of the optical spring may be selected so that it is similar to that of the liquid medium so as to reduce light scatter. The shape of optical spring 158 may be plano, convex, concave or aspheric as required to create the best optical image upon the retinal surface.

Concurrently, the shape of anterior membrane 154 and posterior membrane 156 may be plano, convex, concave or aspheric as required; however, for the preferred embodiment shown, the curvature of the posterior surface of anterior membrane 154 should be roughly equal to that of the anterior surface of optical spring 158 when in its habitual or 'dis- tended' state. The curvature of the anterior surface of posterior membrane 156 should be roughly equal to that of the posterior surface of optical spring 158 when it is in its flattest or 'extended' state. This configuration of shapes allows for all optical surfaces of resilient optical interface 150 to change in unison with minimal optical distortion.

Anterior membrane 154 should be made of materials which are resistant to bio-film adhesion (rubber for example becomes cloudy). Various hydro-phylic elastomers, polyethylene, and polyurethane based polymers are examples of material types suitable for the task. Alternatively, optical spring 158 may be shaped so that its anterior curvature matches that of the posterior surface of optical shield 146. If the refractive index of the fluid within resilient optical interface 150 is greater than that of the fluid that presses posterior membrane 156 forward, then it is possible to design liquid optical systems which operate by the same principles illustrated by the pneumatic lens as disclosed in U.S. provisional patent application No. 60/955,619. Fluid within resilient optical interface 150 may occupy enough space so as to flatten the curvature of posterior membrane 156 when the eye is in its distended state. Posterior membrane 156 then bulges forward to create a minus lens power when the eye is in its extended state.

Figure 12A:
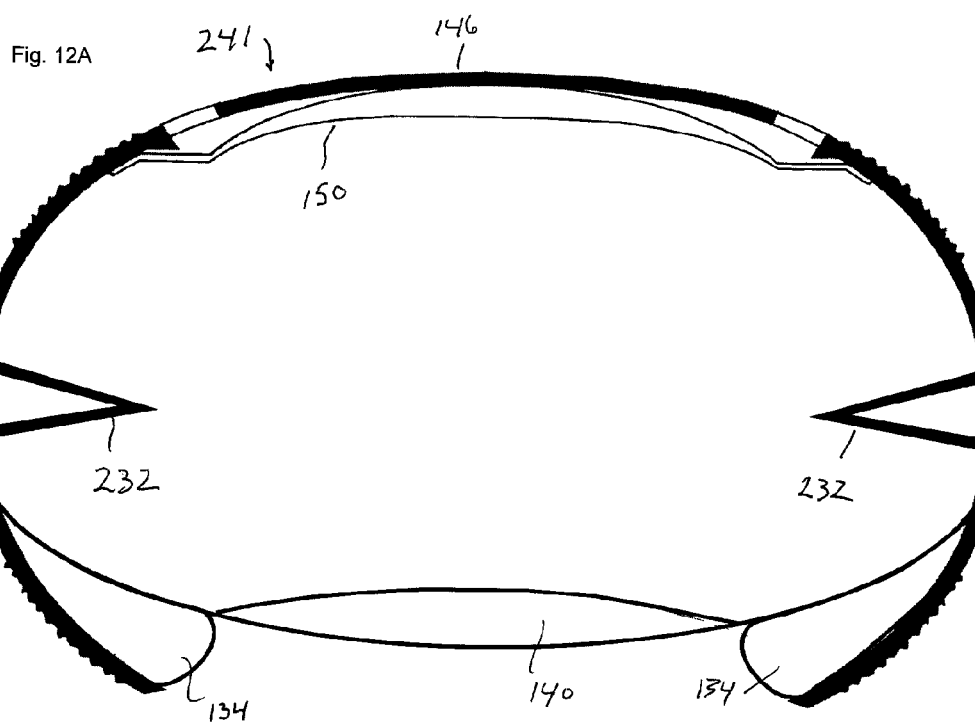
FIG. 12A is a vertical cross section of an embodiment of an inflatable lens/lens retainer which illustrates a billow as it involutes toward the center of the inflatable retainer.
Figure 12B:
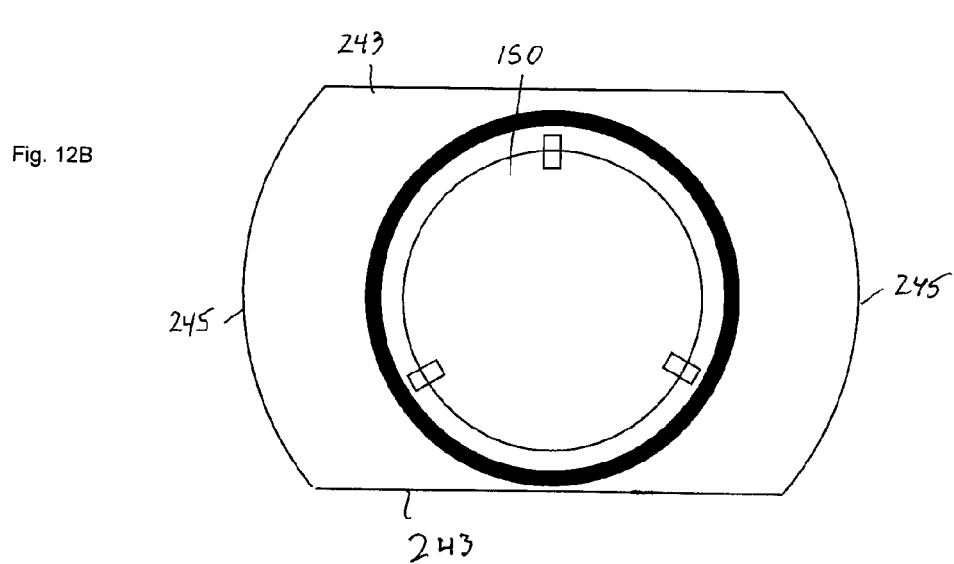
FIG. 12B is a front view of a further embodiment of the invention.

FIG. 12A is a cross sectional view of an inflatable lens/lens retainer which illustrates billow 232 as it involutes toward the center of the inflatable retainer 241. As a consequence of this feature, the inflatable retainer may be truncated as shown on FIG. 12B which is a frontal view of inflatable retainer 241. The truncation of inflatable retainer 241 along edges 243 allows for it to be rolled up into a smaller length, with its axis perpendicular to the truncation, for simplified insertion into the eye. The remaining regions 245 of the outer perimeter of inflatable retainer 241 may be 'scalloped' with indentations or regular extensions to provide rotational stability should astigmatic corrections be incorporated within the optical interfaces of the device.

While a number of exemplary aspects and embodiments have been discussed above, those of skill in the art will recognize certain modifications, permutations, additions and sub-combinations thereof. It is therefore intended that the invention be interpreted to include all such modifications, permutations, additions and sub-combinations as are within their true spirit and scope.

What is claimed is:

1. An inflatable intra ocular lens/lens retainer for implantation into the intra-capsular space of the lens capsule of an aphakic eye, said lens capsule having a posterior lens capsule and an anterior lens capsule, said inflatable intra ocular lens/lens retainer comprising:
   i) an anterior annular expandable intra ocular retainer of deformable material for implantation directly behind the anterior lens capsule, said anterior intra ocular retainer having an anterior surface, a posterior surface, a central space, and a transparent lens support element in the shape of a diaphragm that stretches across the anterior surface of the anterior inflatable intra ocular retainer, said anterior intra ocular retainer sized when expanded to bear directly or indirectly against the inner surface of said anterior lens capsule;
   ii) a posterior annular expandable intra ocular retainer of deformable material for implantation directly in front of the posterior lens capsule, said posterior intra ocular retainer having an anterior surface, a posterior surface, a central space, and a transparent lens support element in the shape of a diaphragm that stretches across the anterior surface of the posterior inflatable intra ocular retainer for engaging the posterior surface of an optical element, said posterior intra ocular retainer sized when expanded to bear directly or indirectly against the inner surface of said posterior lens capsule;

iii) a resilient optical element arranged in said central space of said anterior intra ocular retainer and configured along the visual axis of the eye to provide accommodation in combination with said intra ocular retainers in response to changes of ciliary muscle tone, said resilient optical element comprising an inflatable body of elastically deformable material forming a hollow interior chamber, and having an anterior surface and a posterior surface and a central transparent optical zone, and means for inflating said inflatable body with a transparent optical fluid; and iv) means for expanding each of said anterior and posterior annular expandable intra ocular retainers with a fluid, wherein said means for expanding comprises a filling port communicating with a hollow interior chamber within each of said expandable intra ocular retainers;

wherein when said posterior annular expandable intra ocular retainer is implanted and expanded its posterior surface bears directly or indirectly against the posterior lens capsule of said lens capsule thereby applying pressure against said posterior lens capsule of said lens capsule.

2. The inflatable intra ocular lens/lens retainer of claim 1 wherein said fluid is transparent.

3. The inflatable intra ocular lens/lens retainer of claim 1 wherein said deformable material is non-permeable.

4. The inflatable intra ocular lens/lens retainer of claim 3 wherein said fluid is a gas.

5. The inflatable intra ocular lens/lens retainer of claim 4 wherein said gas has a pressure equal to or greater than atmospheric pressure.

6. The inflatable intra ocular lens/lens retainer of claim 4 wherein said gas is an inert gas of large molecular weight.

7. The inflatable intra ocular lens/lens retainer of claim 6 wherein said gas is selected from the group consisting of perflurocarbon gas, sulfurhexafluoride gas and air.

8. The inflatable intra ocular lens/lens retainer of claim 1 wherein said deformable material is semi-permeable.

9. The inflatable intra ocular lens/lens retainer of claim 8 further comprising osmotic agents within said expandable anterior and posterior retainers to induce osmotic pressure.

10. The inflatable intra ocular lens/lens retainer of claim 1 wherein said expandable intra ocular retainers comprise a liquid-absorptive material which absorbs intra-ocular fluid to thereby expand said expandable intra ocular retainers.

11. The inflatable intra ocular lens/lens retainer of claim 1 wherein said fluid is selected from the group consisting of hydrophilic polymers, glycerin and solutions of visco-elastics, polysaccharides, cellulose and intra ocular fluid.

12. The inflatable intra ocular lens/lens retainer of claim 1 further comprising a shield member positioned between said posterior retainer and said posterior lens capsule to protect the inner surface of said posterior retainer.

13. The inflatable intra ocular lens/lens retainer of claim 1 further comprising an integrated suspension system.

14. The inflatable intra ocular lens/lens retainer of claim 13 wherein said integrated suspension system comprises a plurality of radially extending flanges adapted to fit into the inner surface of the equator of the lens capsule hingedly connected circumferentially around the equator of said inflatable intra ocular lens/lens retainer to thereby suspend said inflatable intra ocular lens/lens retainer centrally along the optical axis of said lens capsule.

15. The inflatable intra ocular lens/lens retainer of claim 13 wherein said integrated suspension system comprises an inflatable annular cushion to position and support said lens/lens retainer.

16. The inflatable intra ocular lens/lens retainer of claim 1 further comprising a flexible membrane shield attached in front of said anterior surface of said anterior retainer to protect the anterior lens capsule, comprising a central opening and a plurality of projections extending radially away from said central opening.

17. The inflatable intra ocular lens/lens retainer of claim 1 further comprising a transparent optical shield on the anterior surface of said anterior retainer, said shield having a surface shaped to provide for vision correction and optical resolution.

18. The inflatable intra ocular lens/lens retainer of claim 1 further comprising a gas releasing, laser absorptive material within a hollow interior of said expandable intra ocular retainers, for expanding said retainers after implanting.

19. The inflatable intra ocular lens/lens retainer of claim 18 wherein said laser absorptive material is a collagen or carbamide.

20. The inflatable intra ocular lens/lens retainer of claim 1 further comprising means for engaging an intra ocular suspension system.

* * * * *